(12) United States Patent
Kim et al.

(10) Patent No.: US 8,784,325 B2
(45) Date of Patent: Jul. 22, 2014

(54) APPARATUS AND METHOD FOR MEASURING BLOOD PRESSURE

(75) Inventors: Youn-ho Kim, Yongin-si (KR); Kun-soo Shin, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 416 days.

(21) Appl. No.: 12/418,903

(22) Filed: Apr. 6, 2009

(65) Prior Publication Data

US 2010/0113946 A1     May 6, 2010

(30) Foreign Application Priority Data

Nov. 3, 2008   (KR) .......................... 10-2008-0108532

(51) Int. Cl.
| | |
|---|---|
| *A61B 5/02* | (2006.01) |
| *A61B 5/022* | (2006.01) |
| *A61B 5/0225* | (2006.01) |
| *A61B 5/021* | (2006.01) |
| *A61B 5/024* | (2006.01) |

(52) U.S. Cl.
CPC ............. *A61B 5/022* (2013.01); *A61B 5/02255* (2013.01); *A61B 5/021* (2013.01); *A61B 5/024* (2013.01)
USPC ............................. 600/493; 600/485; 600/500

(58) Field of Classification Search
USPC ................... 600/483, 484, 490–496, 500–503
See application file for complete search history.

(56) References Cited

U.S. PATENT DOCUMENTS

| | | | | |
|---|---|---|---|---|
| 4,896,676 A | * | 1/1990 | Sasaki ............................ | 600/494 |
| 2004/0210143 A1 | * | 10/2004 | Gallant et al. ................. | 600/485 |
| 2006/0155196 A1 | * | 7/2006 | Ramsey ......................... | 600/490 |
| 2008/0312544 A1 | * | 12/2008 | Mochizuki ..................... | 600/492 |

FOREIGN PATENT DOCUMENTS

| | | |
|---|---|---|
| JP | 09-299340 A | 11/1997 |
| JP | 11-146868 A | 6/1999 |
| KR | 100133448 B1 | 12/1997 |

OTHER PUBLICATIONS

Yong and Geddes, "The Effect of Cuff Pressure Rate on Accuracy in Indirect Measurement of Blood Pressure with the Auscultatory Method," 1987, Jounal of Clinical Monitoring vol. 3, No. 3, pp. 155-159.*
Pessenhofer, "Single cuff comparison of two methods for indirect measurement of arterial blood pressure: standard auscultatory method versus automatic oscillometric method," 1985, Basic Res Cardiol, 81: 101-109.*

* cited by examiner

*Primary Examiner* — Navin Natnithithadha
*Assistant Examiner* — Eric Messersmith
(74) *Attorney, Agent, or Firm* — Cantor Colburn LLP (57) ABSTRACT

Provided are an apparatus and method for measuring blood pressure. The blood pressure measuring apparatus includes a pressure sensor detecting a sphygmus wave and pressure of a blood vessel in a subject, a pulse detecting unit detecting a peak-to-peak interval of the sphygmus wave of the subject, an optimum rate of pressure change detecting unit detecting an optimum rate of pressure change of the blood vessel by using the peak-to-peak interval of the sphygmus wave, a compression unit performing a compression operation in which the blood vessel is compressed at the optimum rate of pressure change detected by the optimum rate of pressure change detecting unit, or a decompression operation in which the blood vessel is compressed so as to be closed, and is then decompressed at the optimum rate of pressure change, and a blood pressure detecting unit detecting blood pressure of the subject, based on the sphygmus wave and the pressure of the blood vessel, which are detected in the compression operation or the decompression operation.

15 Claims, 9 Drawing Sheets

APPARATUS AND METHOD FOR MEASURING BLOOD PRESSURE

CROSS-REFERENCE TO RELATED APPLICATIONS

This application claims priority to Korean Patent Application No. 10-2008-0108532, filed on Nov. 3, 2008, and all the benefits accruing therefrom under 35 U.S.C. §119, the contents of which in its entirety are herein incorporated by reference.

BACKGROUND

1. Field

Disclosed herein is an apparatus and a method for measuring blood pressure in terms of the pulse characteristics of a subject.

2. Description of the Related Art

Various types of blood pressure measuring apparatuses have been developed due to an increasing public interest in health. Blood pressure measuring methods include a Korotkoff-sounds method, an oscillometric method, a tonometric method, and the like. The Korotkoff-sounds method, which is a typical blood pressure measuring method, measures the systolic pressure at which a sound of the pulse of a living being is first heard and the diastolic pressure at which the sound of the pulse is barely audible during a decompression process where the blood flow is blocked by sufficiently compressing a body part through which arterial blood flows.

The oscillometric method and the tonometric method are used for digital blood pressure measuring apparatuses. The oscillometric method detects a sphygmus wave, which occurs in a decompression process after sufficiently compressing a body part through which arterial blood flows so as to block arterial blood flow in a manner that is similar to the Korotkoff-sounds method, or in a compression process in which the body part is compressed at a predetermined compression speed. A pressure at which the amplitude of the sphygmus wave is at a specific level may be measured as a systolic pressure or as a diastolic pressure. Alternatively, a pressure at which the amplitude of the sphygmus wave changes suddenly may be measured as a systolic pressure or as a diastolic pressure.

During the decompressing process after compressing the body part at a predetermined compression speed, a systolic pressure is measured prior to a point in time at which the amplitude of the sphygmus wave is at a maximum, and a diastolic pressure is measured after a point of time at which the amplitude of the sphygmus wave is at the maximum. On the other hand, during the compression process in which the body part is compressed at a predetermined compression speed, the systolic pressure is measured after the point of time at which the amplitude of the sphygmus wave is at the maximum, and the diastolic pressure is measured prior to the point of time at which the amplitude of the sphygmus wave is at the maximum. The tonometric method compresses a body part so that arterial blood flow is not completely blocked and continuously measures blood pressure by using the size and form of a sphygmus wave generated by compressing the body part.

In the oscillometric method, a compression speed or a decompression speed is approximately determined based on a person having a normal pulse. However, when blood pressure of a subject having a slower than normal pulse is measured using the oscillometric method, since the number of peaks of a sphygmus wave is insufficient to measure an accurate blood pressure, it is difficult to ensure the accuracy of the measured blood pressure. On the other hand, when blood pressure of a subject having a faster than normal pulse is measured using the oscillometric method, since there are too many sphygmus wave peaks, it takes a long time to measure blood pressure.

SUMMARY

Disclosed herein is an apparatus and method for measuring blood pressure, which can ensure reliable accuracy regardless of differences in the pulse of a subject.

Additional aspects will be set forth in part in the description which follows and, in part, will be apparent from the description.

To achieve the above and/or other aspects, one or more embodiments may include a blood pressure measuring apparatus including a pressure sensor for detecting a sphygmus wave and pressure of a blood vessel in a subject; a pulse detecting unit for detecting a peak-to-peak interval of the sphygmus wave of the subject, which is detected by the pressure sensor; an optimum rate of pressure change detecting unit for detecting an optimum rate of pressure change of the blood vessel by using the peak-to-peak interval of the sphygmus wave; a compression unit for performing a compression operation in which the blood vessel is compressed at the optimum rate of pressure change; the pressure change being detected by the optimum rate of pressure change detecting unit, or a decompression operation in which the blood vessel is compressed so as to be closed, and is then decompressed at the optimum rate of pressure change; and a blood pressure detecting unit for detecting blood pressure of the subject, based on the sphygmus wave and the pressure of the blood vessel, which are detected in the compression operation or the decompression operation.

In one embodiment, the pressure sensor is in operative communication with the pulse detecting unit, the optimum rate of pressure change detecting unit, the compression unit and the blood pressure detecting unit.

In order to detect the peak-to-peak interval of the sphygmus wave, the compression unit may compress the blood vessel at a constant pressure so that the blood vessel is not closed.

The blood pressure detecting unit may detect the blood pressure of the subject by using an oscillometric method.

The blood vessel may be a radial artery of the wrist.

The blood pressure measuring apparatus may further include a wrist band attached around the subject's wrist.

The optimum rate of pressure change detecting unit may detect the optimum rate of pressure change of the blood vessel by using information that the peak-to-peak interval of the sphygmus wave is inversely proportional to the optimum rate of pressure change of the blood vessel.

The blood pressure measuring apparatus may further include a compression unit controlling unit for determining an optimum value of a control variable for driving the compression unit so that the compression unit is driven to correspond to the optimum rate of pressure change of the blood vessel.

The compression unit controlling unit may detect a plurality of values of the rate of pressure change of the blood vessel respectively corresponding to a plurality of values of the control variable, which are different from each other, may determine a formula representing a relation between the control variable and the rate of pressure change of the blood vessel by using the plurality of values of the rate of pressure change of the blood vessel, and may determine an optimum value of the control variable by substituting the optimum rate of pressure change for the rate of pressure change of the blood vessel in the formula.

The control variable may be any one of a duty ratio, a current value and a voltage value of a signal input to the compression unit in order to drive the compression unit.

To achieve the above and/or other aspects, one or more embodiments may include a blood pressure measuring method including a pulse detecting operation in which a peak-to-peak interval of a sphygmus wave of a subject is detected from the sphygmus wave of the subject; an optimum rate of pressure change detecting operation in which an optimum rate of pressure change of a blood vessel is detected using the peak-to-peak interval of the sphygmus wave; a compression operation in which the blood vessel is compressed at the optimum rate of pressure change, or in a decompression operation in which the blood vessel is compressed so as to be closed, and is then decompressed at the optimum rate of pressure change; and a blood pressure detecting operation in which blood pressure of the subject is detected based on the sphygmus wave and the pressure of the blood vessel of the subject, which are detected during the compression operation.

The pulse detecting operation may include compressing the blood vessel at a constant pressure so that the blood vessel of the subject is not closed.

The pulse detecting operation may include detecting the blood pressure of the subject by using an oscillometric method.

The optimum rate of the pressure change detecting operation may include detecting the optimum rate of pressure change of the blood vessel by using information that the peak-to-peak interval of the sphygmus wave is inversely proportional to the optimum rate of pressure change of the blood vessel.

The compression operation may be performed by a compression unit, and the compression operation may further include determining an optimum value of a control variable for driving the compression unit so that the compression unit is driven to correspond to the optimum rate of pressure change of the blood vessel.

The determining of an optimum value for a control variable may comprise detecting a plurality of values of the rate of pressure change of the blood vessel respectively corresponding to a plurality of values of the control variable. These values of the control variable are different from each other. Following this a formula is determined that represents a relationship between the control variable and the rate of pressure change of the blood vessel by using the plurality of values of the rate of pressure change of the blood vessel, and determining an optimum value of the control variable by substituting the optimum rate of pressure change for the rate of pressure change of the blood vessel in the formula.

To achieve the above and/or other aspects, one or more embodiments may include a blood pressure measuring method including a pulse detecting operation in which a peak-to-peak interval of a sphygmus wave of a subject is detected from the sphygmus wave of the subject; a compression operation in which a blood vessel of the subject at an optimum rate of pressure change corresponding to the peak-to-peak interval of the sphygmus wave, or a decompression operation in which the blood vessel is compressed so as to be closed, and is then decompressed at the optimum rate of pressure change corresponding to the peak-to-peak interval of the sphygmus wave; and a blood pressure detecting operation in which blood pressure of the subject is detected based on the sphygmus wave and the pressure of the blood vessel of the subject, which are detected during the compression operation, wherein, when the peak-to-peak interval of the sphygmus wave of the subject is longer than that of a person having a normal pulse, the optimum rate of pressure change of the subject is shorter than that of the person having the normal pulse, and when the peak-to-peak interval of the sphygmus wave of the subject is less than that of the person having the normal pulse, the optimum rate of pressure change of the subject is more than that of the person having the normal pulse.

BRIEF DESCRIPTION OF THE DRAWINGS

These and/or other aspects, advantages and features of the invention will become apparent by describing in further detail exemplary embodiments thereof with reference to the attached drawings, in which:

FIG. 7A is a graph where the blood pressure measuring method disclosed herein is not used, while FIG. 7B is a graph where the blood pressure measuring method disclosed herein is used; FIG. 8A is a graph where the blood pressure measuring method disclosed herein is not used, and FIG. 8B is a graph where the blood pressure measuring method disclosed herein is used.

DETAILED DESCRIPTION

Aspects, advantages, and features of the present invention and methods of accomplishing the same may be understood more readily by reference to the following detailed description of preferred embodiments and the accompanying drawings. The present invention may, however, may be embodied in many different forms, and should not be construed as being limited to the embodiments set forth herein. Rather, these embodiments are provided so that this disclosure will be thorough and complete and will fully convey the concept of the invention to those skilled in the art, and the present invention will only be defined by the appended claims. Like reference numerals refer to like elements throughout the specification.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the present invention.

Spatially relative terms, such as "below", "lower", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, generally have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the present invention will be described in detail with reference to the accompanying drawings. However, the aspects, features, and advantages of the present invention are not restricted to the ones set forth herein. The above and other aspects, features and advantages of the present invention will become more apparent to one of ordinary skill in the art to which the present invention pertains by referencing a detailed description of the present invention given below FIG. 1 is an exemplary schematic cross-sectional view of a blood pressure measuring apparatus 100.

Figure 1:
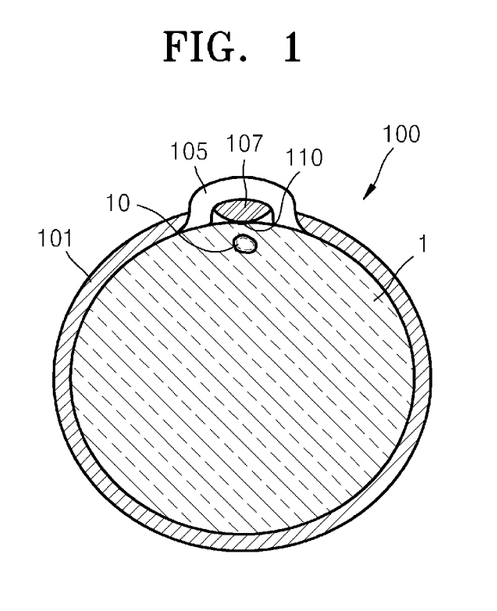
FIG. 1 is an exemplary schematic cross-sectional view of a blood pressure measuring apparatus.

Referring to FIG. 1, the blood pressure measuring apparatus 100 is designed for a wrist 1 through which the radial artery 10 is disposed, so as to facilitate detecting a sphygmus wave and pressure of a blood vessel. The blood pressure measuring apparatus 100 comprises a wrist band 101 that is attached around the wrist 1 of a subject and a blood pressure measuring block 105 for measuring blood pressure. The blood pressure measuring block 105 comprises a compression unit for compressing the radial artery 10 of the wrist 1 that is being subjected to measurement. The compression unit comprises a compression member 107 that is projected toward the wrist 1 from the blood pressure measuring block 105 and an actuator 108 (see FIG. 3) that drives the compression member 107 to be projected or contracted. A pressure sensor 110 that detects the sphygmus wave and pressure of the radial artery 10 is disposed at the ends of the compression member 107 contacting the wrist 1.

Figure 2:
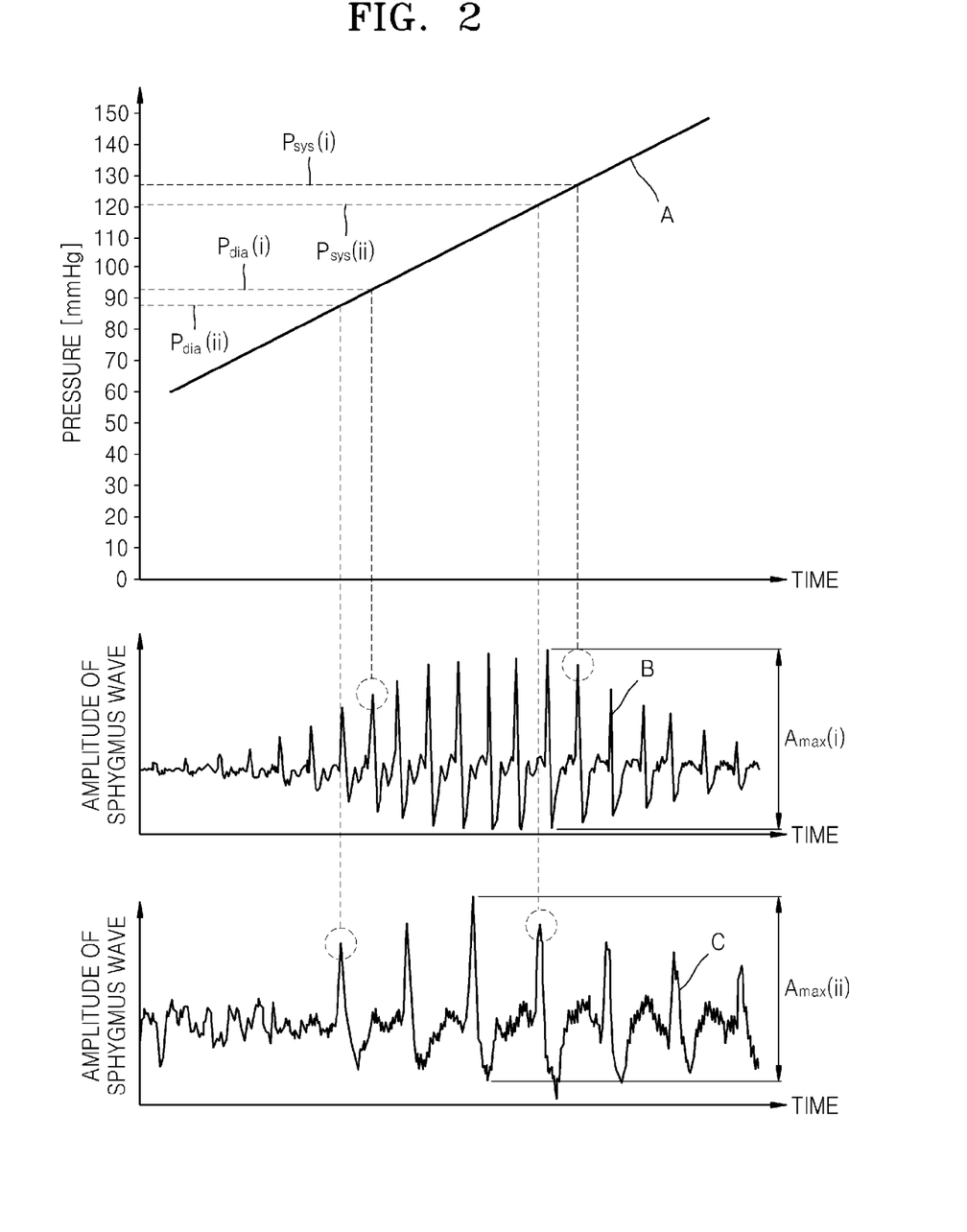
FIG. 2 is a graph of a sphygmus wave detected when blood pressure is measured using an oscillometric method, where line 'A' is a waveform of a compression pressure, line 'B' is a sphygmus waveform of a subject having a normal pulse, and line 'C' is a sphygmus waveform of a subject having a slower than normal pulse.

FIG. 2 is a graph of a sphygmus wave detected when blood pressure is measured using an oscillometric method. The line 'A' is a waveform of a compression pressure. The line 'B' is a sphygmus waveform of a subject having a normal pulse. The line 'C' is a sphygmus waveform of a subject having a slower than normal pulse.

With reference to the line 'A' of FIG. 2, when blood pressure is measured using an oscillometric method, the compression member 107 (see FIG. 1) of the blood pressure measuring apparatus 100 (see FIG. 1) compresses the radial artery 10 (see FIG. 1) at a predetermined rate of pressure change. During this measurement, the waveform of the sphygmus wave of the subject having the normal pulse is the line 'B'. The predetermined rate of pressure change is determined at a rate that is commensurate with a pressure change per peak-to-peak interval (between a pair of adjacent high peaks) of 3 millimeters of mercury (mm Hg) or less. When the change in pressure per peak-to-peak interval is more than 3 mm Hg, the accuracy of the measured blood pressure deteriorates.

In the line 'B', at a predetermined time after reaching a maximum amplitude Amax(i), a pressure detected by the pressure sensor 110 (see FIG. 1) is determined to be the systolic pressure Psys(i) of the subject displaying a normal pulse. In addition, at a predetermined time prior to reaching the maximum amplitude Amax(i), the pressure detected by the pressure sensor 110 (see FIG. 1) is determined to be the diastolic pressure Pdia(i) of the subject displaying the normal pulse. The systolic pressure Psys(i) or the diastolic pressure Pdia(i) may be determined as a pressure at which the amplitude of the sphygmus wave is at a specific level, or alternatively, may be determined as a pressure at which the slope of an envelope line of the sphygmus wave changes suddenly.

Even if the radial artery 10 (see FIG. 1) is compressed at the predetermined rate of pressure change of the line 'A', when a subject has a slower than normal pulse, as shown in the line 'C', a peak-to-peak interval between a pair of adjacent peaks of the line 'C', is greater than that of the line 'B', and a pressure change per peak-to-peak interval between a pair of adjacent peaks of the line 'C' is more than 3 mm Hg. In the line 'C', at a predetermined time after reaching a maximum amplitude Amax(ii), a pressure detected by the pressure sensor 110 (see FIG. 1) is determined to be the systolic pressure Psys(ii) of the subject having a slower-than-normal pulse. In addition, at a predetermined time before reaching the maximum amplitude Amax(ii), a pressure detected by the pressure sensor 110 (see FIG. 1) is determined to be the diastolic pressure Pdia(ii) of the subject having the slower-than-normal pulse.

As a result, as shown in the FIG. 2, when the radial artery 10 (see FIG. 1) is compressed at the same rate of pressure change regardless of a difference in the pulse of a subject, a large error appears in measuring the slower than normal pulse. Illustrated in the FIG. 2 is the case where the radial artery 10 (see FIG. 1) is compressed at the predetermined rate of pressure change. When the radial artery 10 is sufficiently compressed, and then decompressed at the predetermined rate of pressure change, a large error does also appear when measuring the slow pulse of the subject.

Figure 3:
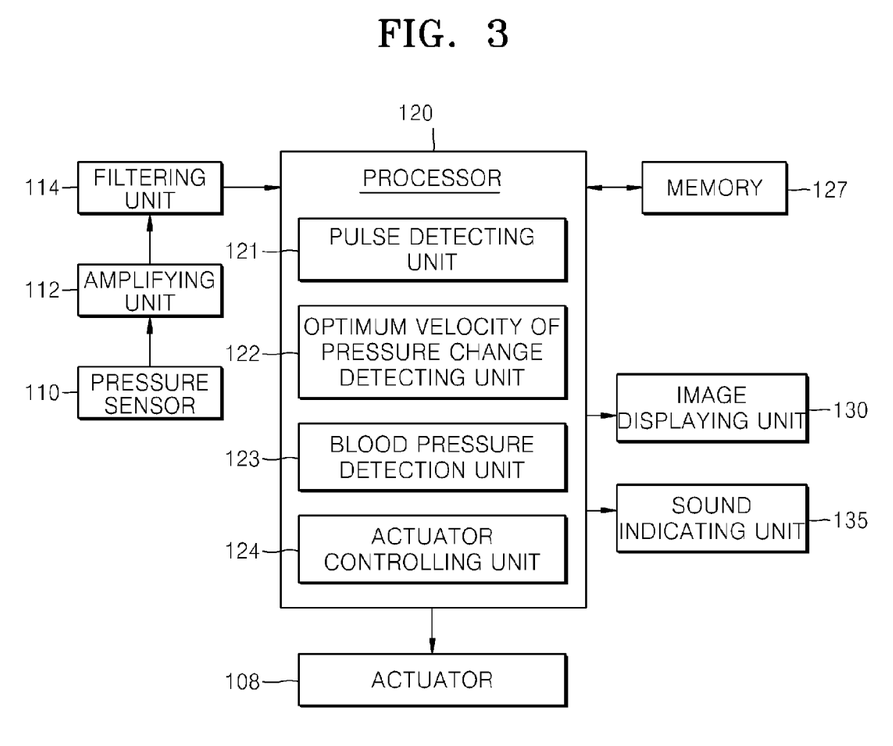
FIG. 3 is an exemplary block diagram of the blood pressure measuring apparatus of FIG. 1.
Figure 4:
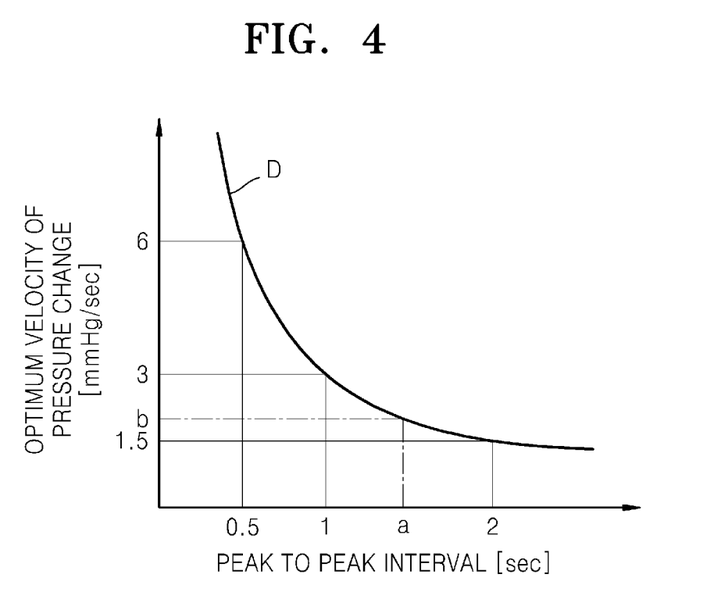
FIG. 4 is a graph showing a relationship between a peak-to-peak interval of a sphygmus wave and an optimum rate of pressure change when a pressure change ratio with respect to the peak-to-peak interval of the sphygmus wave is constantly maintained.
Figure 5:
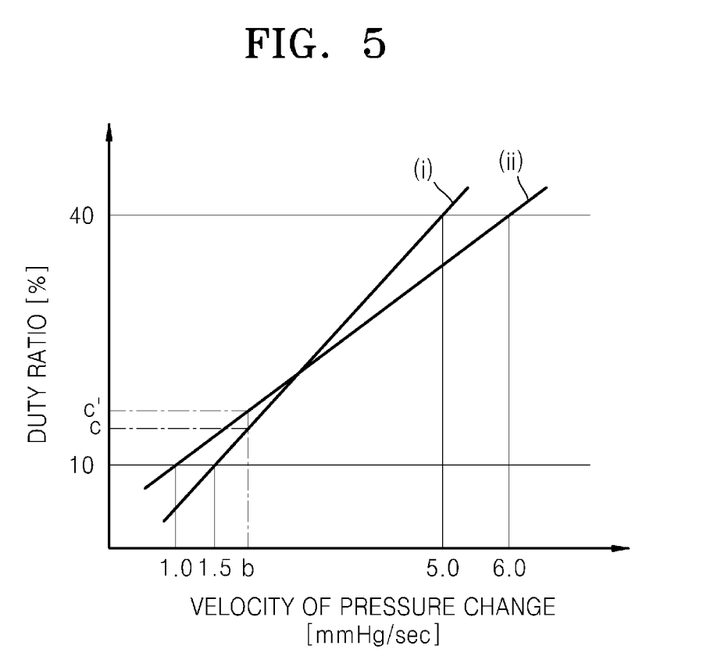
FIG. 5 is a graph showing a relationship between an optimum rate of pressure change, suitable for a subject whose blood pressure is to be measured, and a control variable for maintaining the optimum rate of pressure change.

FIG. 3 is a block diagram of the blood pressure measuring apparatus 100 of FIG. 1. FIG. 4 is a graph showing a relationship between the peak-to-peak interval of a sphygmus wave and an optimum rate of pressure change when a pressure change ratio is maintained at a constant with respect to the peak-to-peak interval of the sphygmus wave. FIG. 5 is a graph showing a relationship between an optimum velocity of pressure change, suitable for a subject when his/her blood pressure is measured, and a control variable for maintaining the optimum velocity of pressure change.

Referring to FIG. 3, the blood pressure measuring apparatus 100 includes the pressure sensor 110 for detecting the sphygmus wave and blood pressure of the subject, an amplifying unit 112 for amplifying a signal generated by the pressure sensor 110, a filtering unit 114 for removing a noise component, a processor 120 for performing a calculation by using the filtered signal, and a memory 127 for storing data and for storing a program used by the processor 120 to perform the calculation. The processor 120 includes a pulse detecting unit 121 for detecting a peak-to-peak interval of the sphygmus wave detected by the pressure sensor 110, an optimum velocity of pressure change detecting unit 122 for detecting the optimum velocity of pressure change of the radial artery 10 (see FIG. 1) by using the peak-to-peak interval of the sphygmus wave, and a blood pressure detection unit 123 for detecting blood pressure of the subject. In addition, the processor 120 further includes an actuator controlling unit 124 for calculating a control variable of the actuator 108 that drives the compression member 107.

The compression member 107 is driven by the actuator 108 and performs a compression operation in which the radial artery 10 is compressed at the optimum rate of pressure change detected by the optimum rate of pressure change detecting unit 122, or a decompression operation in which the radial artery 10 is compressed so as to be closed, and is then decompressed at the optimum rate of pressure change. The actuator controlling unit 124 calculates the control variation of the actuator 108 so that the compression member 107 is driven so as to correspond to the optimum rate of pressure change.

The blood pressure measuring apparatus 100 further includes an image displaying unit 130 for displaying a measured blood pressure so as to be visible, and a sound indicating unit 135 for indicating a proceeding state so as to be audible when the blood pressure is measured. The image displaying unit 130 may include a display panel, and the sound indicating unit 135 may include a speaker.

Referring to FIG. 4, a peak-to-peak interval indicating an interval between a pair of adjacent high peaks during the compression or decompression operations is inversely proportional to the optimum rate of pressure change of the radial artery 10 (see FIG. 1). For example, in the line 'D', a pressure change of the radial artery 10 for a peak-to-peak interval is 3 mm Hg. When a peak-to-peak interval is 1 second, the optimum velocity of pressure change of the radial artery 10 is 3 millimeters of mercury per second ("mm Hg/sec"). When a peak-to-peak interval is 2 seconds, the optimum rate of pressure change of the radial artery 10 is 1.5 mm Hg/sec. In addition, when a peak-to-peak interval is 0.5, the optimum rate of pressure change of the radial artery 10 is 6 mm Hg/sec.

In FIG. 4, when a peak-to-peak interval of a subject is 1 second, his/her pulse rate is normal. Thus, during the compression or decompression operations, when the optimum rate of pressure change of the radial artery 10 is set to be 3 mm Hg/sec, an accurate blood pressure measurement can be obtained. When a peak-to-peak interval of a subject is longer than 1 second, his/her pulse is slower than normal pulse. Thus, during the compression or decompression operations, when the optimum rate of pressure change of the radial artery 10 is set to be less than 3 mm Hg/sec, an accurate blood pressure can be obtained. In the meantime, when a peak-to-peak interval is less than 1 second, his/her pulse is faster than normal pulse. Thus, during the compression or decompression operations, when the optimum rate of pressure change of the radial artery 10 is set to be more than 3 mm Hg/sec, an accurate and speedy measurement of blood pressure can be obtained.

When an operation of the actuator 108 (see FIG. 3) is controlled by using pulse width modulation ("PWM"), the control variable for controlling the operation of the actuator 108 may be a duty ratio of a pulse signal input to the actuator 108. Alternatively, when the operation of the actuator 108 is controlled by a current or voltage, the control variable for controlling the operation of the actuator 108 may be a current or voltage value of a signal input to the actuator 108.

In the meantime, the control variable may vary according to the characteristic of a subject. For example, a duty ratio required to compress the radial artery 10 (see FIG. 1) at the same rate of pressure change may vary according to the flexibility of the subject's skin. A method of calculating a control variable according to the characteristic of a subject will be described with reference to FIG. 5.

Referring to FIG. 5, with respect to a first subject, a duty ratio that is a control variable is set to 10%, and an actual rate of pressure change is measured as 1.0 mmHg/sec when the radial artery 10 is compressed. In addition, the duty ratio is set to 40%, and the actual rate of pressure change is measured as 5.0 mmHg/sec when the radial artery 10 is compressed. By connecting the two measured points, a relation between the duty ratio that is a control variable and the rate of pressure change of the radial artery 10 can be obtained. A line (i) of FIG. 5 is a plot corresponding to the formula determined using the measurement result of the first subject.

With respect to a second subject, a duty ratio is set to 10%, and an actual rate of pressure change is measured as 1.0 mm Hg/sec when the radial artery 10 is compressed. In addition, the duty ratio is set to 40%, and the actual rate of pressure change is measured as 6.0 mm Hg/sec when the radial artery 10 is compressed. By connecting the two measured points, a relation between the duty ratio and the rate of pressure change of the radial artery 10 can be obtained. The line (ii) of FIG. 5 is a plot corresponding to the formula determined using the measurement result of the second subject.

With reference to FIGS. 4 and 5, an example of a method of calculating a control variable of the actuator 108 by using a peak-to-peak interval of a sphygmus wave of a subject, which is obtained by measuring the pulse of the subject, will be described. As shown in FIG. 4, it can be seen that when a peak-to-peak interval of a sphygmus wave of the subject is measured as 'a', an optimum rate of pressure change of the subject is 'b'. If the characteristics of the subject satisfy the formula corresponding to the line (i), the duty ratio that is a control variable is 'c'. The formula corresponding to the characteristics of the subject can be determined by setting the duty ratio as 10% and 40% and measuring pressure change velocities respectively corresponding to 10% and 40%.

The formula corresponding to the characteristics of the subject determined as described above may be a new formula that does not correspond to the line (i) or (ii) of FIG. 5. Although only straight lines corresponding to the formula are illustrated in FIG. 5, a formula corresponding to a curved line can be determined by setting three or more duty ratios and measuring pressure change rates respectively that correspond to the duty ratios. In addition, as described above, the control variable is not limited to only the duty ratio. For example, a current value or a voltage value may also be used.

Figure 6:
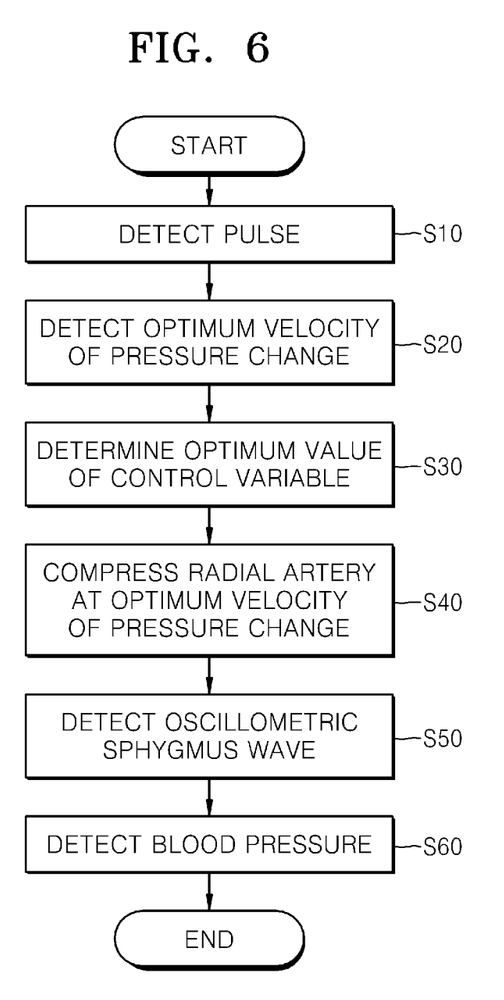
FIG. 6 is a flowchart showing an exemplary blood pressure measuring method.

FIG. 6 is a flowchart showing an exemplary blood pressure measuring method. Hereinafter, the blood pressure measuring method will be described with reference to FIGS. 1, 3 and 6.

In order to measure blood pressure, the wrist band 101 is attached around the wrist 1 to fix the blood pressure measuring apparatus 100. The blood pressure measuring method using the blood pressure measuring apparatus 100 includes a pulse detecting operation (operation S10 in the FIG. 6) in which a peak-to-peak interval of a sphygmus wave of a subject is detected from the sphygmus wave of the subject, an optimum rate of pressure change detecting operation (operation S20) in which the optimum rate of pressure change of the radial artery 10 is detected using the peak-to-peak interval of the sphygmus wave, an operation (operation S30) in which an optimum value of a control variable for driving the actuator 108 is determined, a compression operation (operation S40) in which the radial artery 10 is compressed, an operation (operation S50) in which a oscillometric sphygmus wave is detected during the compression operation (operation S40), and a blood pressure detecting operation (operation S60) in which blood pressure of the subject is detected based on the sphygmus wave of the subject and the pressure of the radial artery 10.

The pulse detecting operation (operation S10) may include a compression operation in which the radial artery 10 is compressed by the compression member 107 at a constant pressure so that the radial artery 10 is not closed. The pulse detecting operation (operation S10) is performed by the pulse detecting unit 121. When the radial artery 10 is compressed by a predetermined pressure, a sphygmus wave in which a high peak and a low peak are alternatively shown is detected by the pressure sensor 110. In addition, by measuring a period of time between a pair of adjacent high peaks in the sphygmus wave, the peak-to-peak interval can be detected.

The optimum rate of pressure change detecting operation (operation S20) is performed by the optimum rate of pressure change detecting unit 122, and the optimum rate of pressure change of the radial artery 10 can be detected using the peak-to-peak interval detected in the operation S10. A method of detecting an optimum rate of pressure change has been described with reference to FIG. 4, and thus its description will not be repeated here.

The operation S30 is performed by the actuator controlling unit 124, and a duty ratio that is a control variable of the actuator may be determined using the optimum rate of pressure change detected in the operation S20. The method of detecting the optimum rate of pressure change has been described with reference to FIG. 5, and thus its description will not be repeated here.

The compression operation (operation S40) is performed by a compression unit including the actuator 108 and the compression member 107. By driving the actuator 108 by using the optimum value of the control variable determined in operation S30, the radial artery 10 is compressed at the optimum rate of pressure change. Alternatively, the radial artery 10 is compressed so as to be closed and is then decompressed at the optimum rate of pressure change. The blood detecting operation (operation S60) is the same as a method for detecting a systolic pressure and a diastolic pressure, which has been described with reference to the line B of FIG. 2, and thus its description will not be repeated here.

Figure 7A:
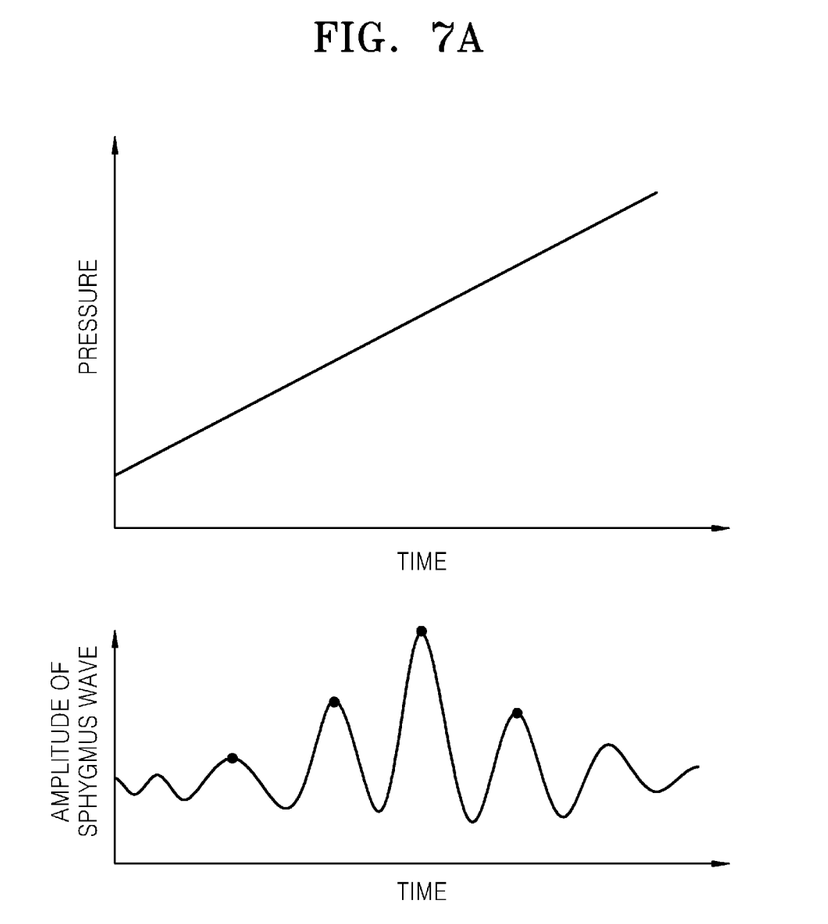
FIGS. 7A and 7B are graphs showing cases where a sphygmus wave is detected when blood pressure is measured using an oscillometric method with respect to a subject having a slower than normal pulse.
Figure 7B:
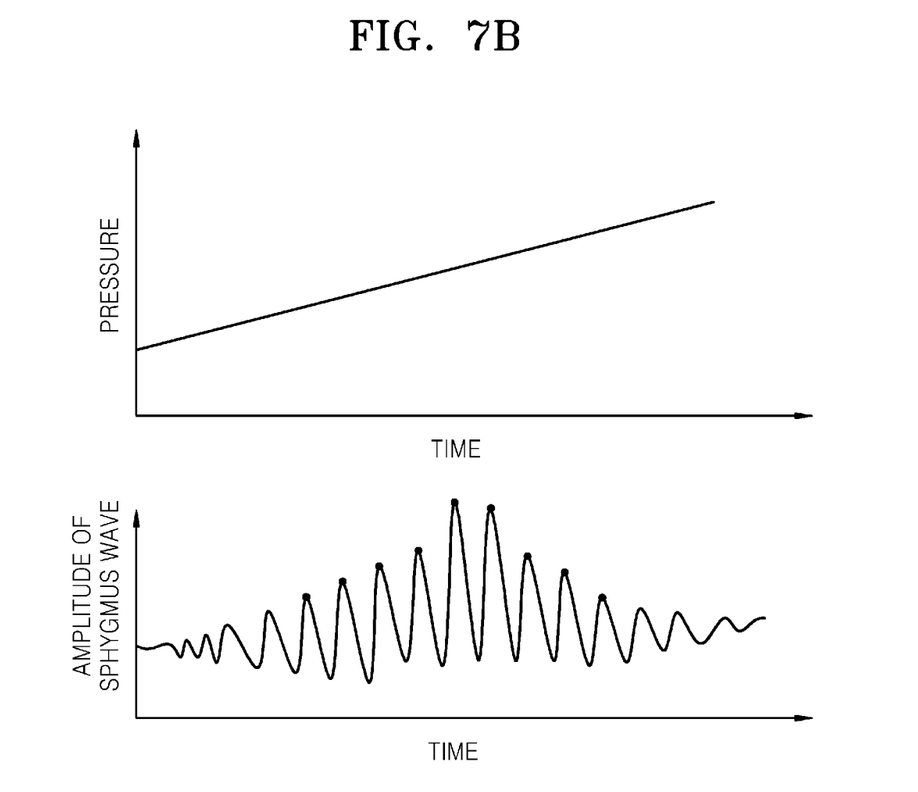

FIGS. 7A and 7B are graphs showing the cases where a sphygmus wave is detected when blood pressure is measured using an oscillometric method with respect to a subject having a slower than normal pulse. FIG. 7A is a graph where the blood pressure measuring method according to the present embodiment is not used. FIG. 7B is a graph where the blood pressure measuring method according to the present embodiment is used. Referring to FIG. 7A, when the radial artery 10 (see FIG. 1) of a subject having the slower than normal pulse is compressed at a predetermined rate of pressure change (e.g., 3 mm Hg/sec) suitable for measuring blood pressure of a subject having the normal pulse, the number of peaks detected from a sphygmus wave during the compressing of the radial artery 10 is not sufficient, and a pressure change per peak-to-peak interval between adjacent high peaks is more than 3 mm Hg. Thus, an accurate blood pressure measurement result cannot be obtained.

Referring to FIG. 7B, when the radial artery 10 of the subject having the slower than normal pulse is compressed at a predetermined rate of pressure change (e.g., a rate less than 3 mm Hg/sec) less than the rate of pressure change used in the case of FIG. 7A, the number of peaks detected from the sphygmus wave during the compressing of the radial artery 10 is sufficient, and a pressure change per peak-to-peak interval between adjacent high peak can be maintained within 3 mm Hg. Thus, an accurate blood pressure measurement result can be obtained.

Figure 8A:
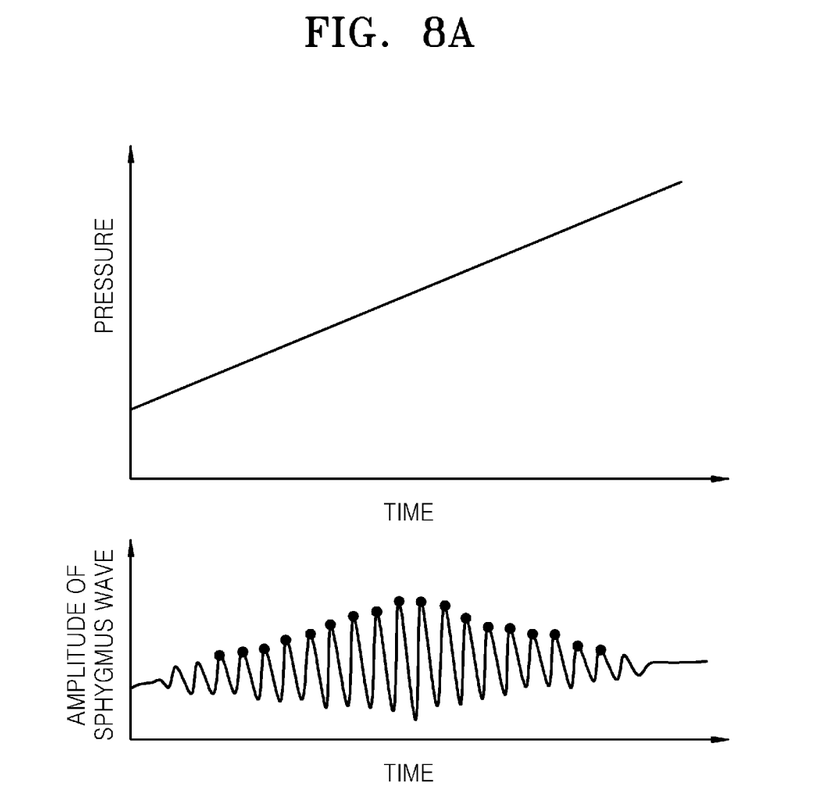
FIGS. 8A and 8B are graphs showing cases where a sphygmus wave is detected when blood pressure is measured using an oscillometric method with respect to a subject having a faster than normal pulse, where
Figure 8B:
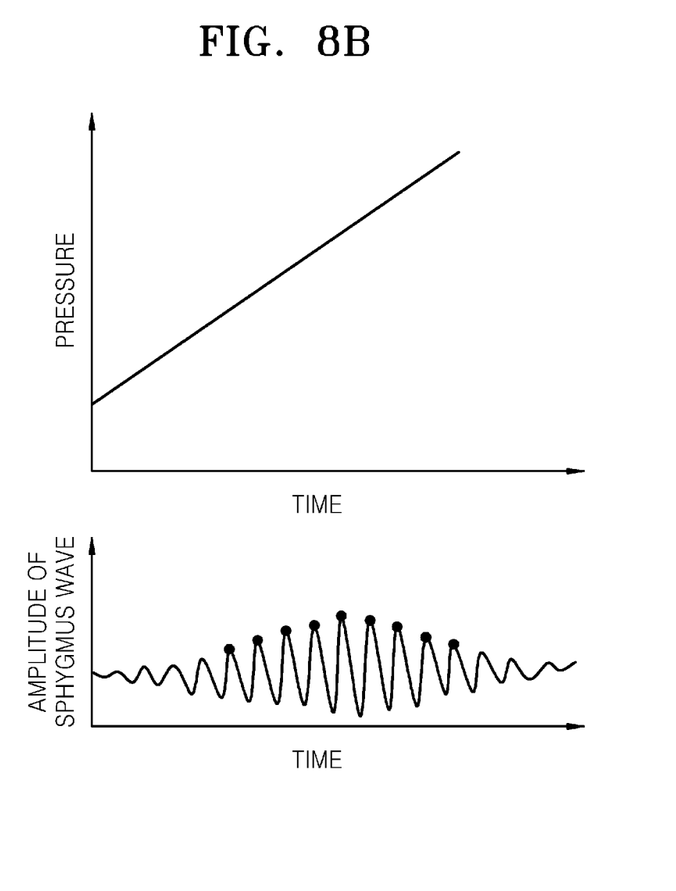

FIGS. 8A and 8B are graphs showing the cases where a sphygmus wave is detected when blood pressure is measured using an oscillometric method with respect to a subject having a faster than normal pulse. FIG. 8A is a graph where the blood pressure measuring method as disclosed herein is not used. FIG. 8B is a graph where the blood pressure measuring method disclosed herein is used. Referring to FIG. 8A, when the radial artery 10 (see FIG. 1) of a subject having the faster than normal pulse is compressed at a predetermined rate of pressure change (e.g., 3 mm Hg/sec) suitable for measuring blood pressure of a subject having the normal pulse, since there are too many peaks detected from a sphygmus wave during the compressing of the radial artery 10, the calculation performed by the processor 120 (see FIG. 3) takes a long time, and the measurement of blood pressure is delayed.

Referring to FIG. 8B, when the radial artery 10 of the subject having the faster than normal pulse is compressed at a predetermined rate of pressure change (e.g., a rate more than 3 mm Hg/sec) more than the rate of pressure change used in the case of FIG. 8A, the number of peaks detected from the sphygmus wave during the compressing of the radial artery 10 is appropriate. Thus, an accurate and speedy blood pressure measurement can be obtained.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A blood pressure measuring apparatus comprising:
a pressure sensor for detecting a sphygmus wave and pressure of a blood vessel in a subject;
a pulse detecting unit for detecting a peak-to-peak interval of the sphygmus wave of the subject, which is detected by the pressure sensor;
an optimum rate of pressure change detecting unit for detecting an optimum rate of pressure change of the blood vessel by using the peak-to-peak interval of the sphygmus wave;
a compression unit for performing a compression operation in which the blood vessel is compressed at the optimum rate of pressure change detected by the optimum rate of pressure change detecting unit, or a decompression operation in which the blood vessel is compressed so as to be closed, and is then decompressed at the optimum rate of pressure change; and
a blood pressure detecting unit for detecting blood pressure of the subject, based on the sphygmus wave and the pressure of the blood vessel, which are detected in the compression operation and the decompression operation; the pressure sensor being in operative communication with the pulse detecting unit, the optimum rate of pressure change detecting unit, the compression unit and the blood pressure detecting unit, and
wherein the optimum rate of pressure change detecting unit detects the optimum rate of pressure change of the blood vessel by using information that the peak-to-peak interval of the sphygmus wave is inversely proportional to the optimum rate of pressure change of the blood vessel.

2. The blood pressure measuring apparatus of claim 1, wherein the compression unit compresses the blood vessel at a constant pressure so that the blood vessel is not closed to detect the peak-to-peak interval of the sphygmus wave.

3. The blood pressure measuring apparatus of claim 1, wherein the blood pressure detecting unit detects the blood pressure of the subject by using an oscillometric method.

4. The blood pressure measuring apparatus of claim 1, wherein the blood vessel is a radial artery of the wrist.

5. The blood pressure measuring apparatus of claim 4, further comprising a wrist band attached around the subject's wrist.

6. The blood pressure measuring apparatus of claim 1, further comprising a compression unit controlling unit for determining an optimum value of a control variable for driving the compression unit so that the compression unit is driven to correspond to the optimum rate of pressure change of the blood vessel.

7. The blood pressure measuring apparatus of claim 6, wherein the control variable is any one of a duty ratio, a current value or a voltage value of a signal input to the compression unit in order to drive the compression unit.

8. The blood pressure measuring apparatus of claim 6, wherein the compression unit controlling unit detects a plurality of values of the rate of pressure change of the blood vessel respectively corresponding to a plurality of values of the control variable, which are different from each other, and which determine a formula representing a relation between the control variable and the rate of pressure change of the blood vessel by using the plurality of values of the rate of pressure change of the blood vessel, and determines an optimum value of the control variable by substituting the optimum rate of pressure change for the rate of pressure change of the blood vessel in the formula.

9. A blood pressure measuring method comprising:
a pulse detecting operation in which a peak-to-peak interval of a sphygmus wave of a subject is detected from the sphygmus wave of the subject;
an optimum rate of pressure change detecting operation in which an optimum rate of pressure change of a blood vessel is detected using the peak-to-peak interval of the sphygmus wave;
a compression operation in which the blood vessel is compressed at the optimum rate of pressure change, or a decompression operation in which the blood vessel is compressed so as to be closed, and is then decompressed at the optimum rate of pressure change; and
a blood pressure detecting operation in which blood pressure of the subject is detected based on the sphygmus wave and the pressure of the blood vessel of the subject, which are detected during the compression operation,
wherein the optimum rate of pressure change detecting unit detects the optimum rate of pressure change of the blood vessel by using information that the peak-to-peak interval of the sphygmus wave is inversely proportional to the optimum rate of pressure change of the blood vessel.

10. The blood pressure measuring method of claim 9, wherein the pulse detecting operation comprises compressing the blood vessel at a constant pressure so that the blood vessel of the subject is not closed.

11. The blood pressure measuring method of claim 9, wherein the pulse detecting operation comprises detecting the blood pressure of the subject by using an oscillometric method.

12. The blood pressure measuring method of claim 9, wherein the blood vessel is a radial artery of the wrist.

13. The blood pressure measuring method of claim 9, wherein the compression operation is performed by a compression unit, and wherein the compression operation further comprises determining an optimum value of a control variable for driving the compression unit so that the compression unit is driven to correspond to the optimum rate of pressure change of the blood vessel.

14. The blood pressure measuring method of claim 13, wherein the control variable is any one of a duty ratio, a current value or a voltage value of an input signal input to the compression unit in order to drive the compression unit.

15. The blood pressure measuring method of claim 13, wherein the determining an optimum value of a control variable comprises detecting a plurality of values of the rate of pressure change of the blood vessel respectively corresponding to a plurality of values of the control variable, which are different from each other, determining a formula representing a relation between the control variable and the rate of pressure change of the blood vessel by using the plurality of values of the rate of pressure change of the blood vessel, and determining an optimum value of the control variable by substituting the optimum rate of pressure change for the rate of pressure change of the blood vessel in the formula.

* * * * *